United States Patent
Notte et al.

(10) Patent No.: US 8,461,088 B2
(45) Date of Patent: Jun. 11, 2013

(54) METHOD OF SCALE INHIBITION

(75) Inventors: Patrick P. B Notte, Wavre (BE); Albert Devaux, Mont-Saint-Guibert (BE); Jan Van Bree, Ottenburg (BE); Tessa Johnson, Sint Amandsbert (BE)

(73) Assignee: Dequest AG, Zug (CH)

( * ) Notice: Subject to any disclaimer, the term of this patent is extended or adjusted under 35 U.S.C. 154(b) by 645 days.

(21) Appl. No.: 12/376,896

(22) PCT Filed: May 25, 2007

(86) PCT No.: PCT/EP2007/004682
§ 371 (c)(1),
(2), (4) Date: May 14, 2009

(87) PCT Pub. No.: WO2008/017338
PCT Pub. Date: Feb. 14, 2008

(65) Prior Publication Data
US 2011/0124533 A1    May 26, 2011

(51) Int. Cl.
C09K 8/60 (2006.01)

(52) U.S. Cl.
USPC .......................................................... 507/235

(58) Field of Classification Search
None
See application file for complete search history.

(56) References Cited

U.S. PATENT DOCUMENTS

| | | | |
|---|---|---|---|
| 4,080,375 A | | 3/1978 | Quinlan |
| 4,869,827 A | * | 9/1989 | Chagnard et al. ............. 210/700 |
| 5,087,376 A | | 2/1992 | Bendiksen et al. |
| 5,112,496 A | | 5/1992 | Dhawan et al. |
| 5,261,491 A | * | 11/1993 | Stewart et al. ................ 166/279 |
| 5,263,539 A | | 11/1993 | Salimi et al. |
| 5,414,112 A | * | 5/1995 | Dragisich ........................ 562/12 |
| 5,531,934 A | * | 7/1996 | Freeman et al. .............. 252/390 |
| 6,022,401 A | | 2/2000 | Tang et al. |
| 2004/0235664 A1 | | 11/2004 | Vandenmersch et al. |
| 2004/0244969 A1 | | 12/2004 | Kotlar et al. |

FOREIGN PATENT DOCUMENTS

| | | |
|---|---|---|
| DE | 141930 | 5/1980 |
| DE | 4131912 | 1/1993 |
| EP | 408297 | 1/1991 |
| GB | 2306465 | 5/1997 |
| WO | 0149756 | 7/2001 |
| WO | 0185616 | 11/2001 |

OTHER PUBLICATIONS

Kunlin Huang, Covalent Bonding of Phosphonates of L-Proline and L-Cysteine to γ-Zirconium Phosphate, Eur. J. Inorg. Chem, 2004, 2956-2960.

* cited by examiner

*Primary Examiner* — Randy Gulakowski
*Assistant Examiner* — Jeffrey Washville
(74) *Attorney, Agent, or Firm* — Husch Blackwell LLP

(57) ABSTRACT

A method is disclosed to inhibit scale formation in aqueous systems whereby a threshold amount of a scale inhibiting agent, represented by an aminoacid alkylphosphonic acid, is added to the aqueous system. The aminoacid moiety can be represented by α-species or by species having, at least, two or more carbon atoms between the carboxylic moiety and the amine group. These aminoacid based inhibitors exhibit unusually superior performance and system acceptability compared to leading state-of-the-art inhibitors.

9 Claims, No Drawings

METHOD OF SCALE INHIBITION

This invention relates to an improved method of scale inhibition, such as barium scale inhibition, which can be useful in connection with oil recovery and water treatment applications. The method broadly comprises the addition of a threshold amount of a selected amino acid alkyl phosphonic acid scale inhibitor. The scale inhibitor, for use in the inventive method, can be selected from α-amino acid alkyl phosphonic acids and from amino acid species having a $C_2$-$C_{20}$ hydrocarbon group connecting the carboxyl and amine moieties. Excluded are specific α-amino acid alkyl phosphonic acids, namely those which are substituted by: selected electron rich moieties containing, at least, one lone pair of electrons; aromatics wherein at least one of the carbon atoms has been substituted by a heteroatom; and compounds wherein the α-carbon atom is substituted by narrowly defined electron withdrawing moieties.

The domain of effectively controlling the formation of inorganic deposits, in particular inhibiting the formation of undesirable levels of the like deposits, including frequently calcium carbonate and barium sulphate, in water is well known and has been around for a long time. As one can consequently expect, the relevant art is fairly crowded.

WO 01/49756 discloses scale inhibitors comprising a hydro soluble copolymer consisting of major amounts of styrene sulfonic acid and vinyl sulfonic acid and, optionally, minor levels of non-ionizable monomers. These inhibitor combinations can be used in a squeeze treatment. U.S. Pat. No. 5,112,496 describes compositions and methods for inhibiting oil field scale formation, particularly in high brine environments. Aminomethylene phosphonates containing 2 or more amine moieties, wherein substantially all of the available N—H functions have been phosphonated, are suitable for use. U.S. Pat. No. 4,080,375 pertains to methylene phosphonates of amino-terminated oxyalkylates, having at least two amino groups, and the use thereof as scale inhibitors in marine oil recovery activities as well as their use for chelation in biological systems. As an example, the phosphonates can effectively sequester iron ions within the context of secondary oil recovery by means of water floods.

U.S. Pat. No. 5,263,539 describes method and composition technology useful for controlling and reducing the occurrence of scale in subterranean formations. The inhibitor compositions comprise an amino phosphonic acid and a copolymer of an alkenyl sulfonic acid compound and an ethylenically unsaturated monomer. The phosphonic acid can be represented by bishexamethylene triamine pentamethylene phosphonic acid. GB 2 306 465 pertains to a method of scale inhibition for use in oil field operations where water can contain high concentrations of alkaline earth metal salts such as barium salts. Preferred scale inhibitors can be represented by hydroxyl alkylated phosphonomethyl amines.

U.S. Pat. No. 6,022,401 discloses biodegradable corrosion inhibitors and anti-scalants for use in oil field fluid systems and other industrial water applications. The corrosion inhibitors/anti-scalants are represented by modified poly(aspartic acid) polymers and modified aspartic acid units. The modified aspartic acid can be substituted by selected side chains such as methyl phosphonic acids/salts.

EP 0 408 297 describes scale inhibitors suitable for inhibiting calcium and barium scale formation in aquatic systems in which iron can be present. The inhibitor is represented by a methylene phosphonate, preferably carboxybisnitrilo tetra (methylene phosphonic acid), also known as urea(tetramethylene phosphonic acid). WO 01/85616 divulges a scale- and corrosion-inhibitor for application, inter alia, in water used in oilfield activities, containing, at least, one oxyalkylene unit and one phosphonate unit. The oxyalkylene can be represented by triethylene glycol or tetraethylene glycol. The phosphonate can be represented by vinyl phosphonic acid or vinylidene diphosphonic acid. In a preferred approach, the phosphonate and the oxyalkylene constituents can be reacted to thus yield a single compound for use.

Kulin Huang et al., Eur. J. Inorg. Chem. 2004, 2956-2960, describe the synthesis of functionalized γ-zirconium phosphate-phosphonates based on N-phosphonomethyl-L-proline from proline and N-phosphonomethyl-1,3-thiazolidine-4-carboxylic acid from cysteine. A method for producing N-phosphonomethylglycine by reaction of hexahydrotriazine with triacyl phosphate is described in WO 2003 000704. Along the same lines, DDR patent 141 930 describes the manufacture of monophosphonated amino acids or the esters thereof. The amino acid moiety can, in the final product, be represented by α-alanine, β-alanine, phenylalanine and asparagine. The purpose of the study was the preparation of monophosphonates having one residual N—H function.

DE 41 31 912 discloses mixtures of carboxyalkane aminomethane phosphonic acids prepared by reacting natural proteins, in particular from waste such as e.g. leather, corn and soya, egg white, skimmed and sugar-free milk powder, wool and silk waste, animal hair and other protein wastes. U.S. Pat. No. 5,087,376 discloses a method of inhibiting the formation of scale-forming salts by means of a low level of diphosphonomethyl derivatives of taurine or cysteic acid.

U.S. Pat. No. 5,414,112 discloses N-bis(phosphonomethyl)amino acids and their use to control calcium carbonate scale in contact with industrial process waters. Specific compounds described are N,N-bis(phosphonomethyl)-L-glutamic acid, N,N-bis(phosphonomethyl)-L-serine and N,N,N',N'-bis(phosphonomethyl)-L-lysine. The L-lysine compound is represented by species carrying one phosphonomethyl moiety attached to one amino radical.

The art, in essence, aims at adding cumulative functionalities to thus secure additive results without providing remedy to known performance deficiencies, particularly within the context of marine oil recovery activities and/or water treatment applications, and/or avoiding multi component systems which are known to exhibit material deficiencies which are inherently attached to such known active combinations.

It is a major object of this invention to provide a beneficial method for scale inhibition capable of effectively limiting scale in aqueous environment under a broad range of conditions including temperature, hardness levels and alkalinity. It is another object of this invention to provide an effective scale control method thereby substantially using a single active scale inhibitor. Another object of the invention aims at providing effective oil scale control without any substantial secondary negatives in relation to e.g. the medium of application. Still another object of this invention aims at providing effective means for water treatment control. Yet another object of this invention concerns a provision of scale control under severe temperature conditions.

The foregoing and other objects of this invention can now be met by the provision of a scale inhibition method comprising the use of threshold amounts of selected alkyl phosphonated amino acids.

The term "percent" or "%" as used throughout this application stands, unless defined differently, for "percent by weight" or "% by weight". The terms "phosphonic acid" and "phosphonate" are also used interchangeably depending, of course, upon medium prevailing alkalinity/acidity conditions. The term "threshold" is well known in the water treatment domain. The ability of very small amounts of scale inhibitors to keep large quantities of scalants in solution is known as the "threshold effect". Or in other words, it is the prevention of precipitation from supersaturated solutions of scalants by ppm levels of inhibitor. The term "ppm" stands for "parts per million".

A beneficial method for effectively controlling the formation of inorganic deposits, in particular the inhibition of earth alkali metal scale, has now been discovered. In more detail, the method in accordance with this invention concerns scale control in aqueous systems adding a threshold amount of a scale inhibiting agent selected from the group of:

i. aminoacid alkylphosphonic acids having the formula $$A^1\text{-}(B)_x$$

wherein $A^1$ has the formula $$HOOC\text{-}A\text{-}NH_2$$

wherein A is independently selected from $C_2$-$C_{20}$ linear, branched, cyclic or aromatic hydrocarbon chains, optionally substituted by $C_1$-$C_{12}$ linear, branched, cyclic or aromatic hydrocarbon groups, optionally substituted by OH, COOH and/or $NH_2$ moieties, and B is an alkylphosphonic acid moiety having from 1 to 6 carbon atoms in the alkyl group and x is an integer of from 1 to 10, preferably from 1 to 6, ii. aminoacid alkylphosphonic acids having the formula $$A^2\text{-}B_y$$

wherein $A^2$ has the formula $$HOOC\text{—}C(NH_2)(R)(R')$$

wherein R and R' are independently selected from $C_1$-$C_{20}$ linear, branched, cyclic or aromatic hydrocarbon chains, optionally substituted by $C_1$-$C_{12}$ linear, branched, cyclic or aromatic hydrocarbon groups, optionally substituted by OH, $NH_2$ and/or COOH, and one of R or R' can be hydrogen with the proviso of excluding:
compounds wherein R and/or R' are electron rich moieties containing, at least, one lone pair of electrons, which moiety is directly attached to an aromatic moiety by a covalent bond; or aromatics wherein at least one of the carbon atoms has been substituted by a heteroatom; and compounds, in the event R is —C(X)(R")(R"') and R', R" and R"' are hydrogen wherein X is an electron withdrawing group selected from $NO_2$, CN, COON, $SO_3H$, OH and halogen, with the further proviso that when:

$A^2$ is L-lysine, at least one L-lysine amino radical carries 2 (two) alkyl phosphonic acid moieties; and when $A^2$ is L-glutamic acid, the term glutamic acid phosphonate represents a combination of from 50-90% by weight pyrrolidone carboxylic acid N-methylene phosphonic acid and from 10-50% by weight of L-glutamic acid diphosphonic acid, expressed on the basis of the reaction products; and B is an alkylphosphonic acid moiety having from 1 to 6 carbon atoms in the alkyl group and y is an integer in the range of from 1 to 10, preferably from 1 to 6, A first essential aminoacid alkylphosphonic acid for use in the method of this invention can be represented by the formula:

$$A^1\text{-}(B)_x$$

wherein $A^1$ has the formula $$HOOC\text{-}A\text{-}NH_2$$

wherein A is independently selected from $C_2$-$C_{20}$ linear, branched, cyclic or aromatic hydrocarbon chains, (said chains being) optionally substituted by $C_1$-$C_{12}$ linear, branched, cyclic or aromatic hydrocarbon groups, (said groups and/or chains being) optionally substituted by OH, COOH and/or $NH_2$ moieties. In a preferred execution, A can be represented by a $C_2$-$C_{16}$ linear hydrocarbon chain, optionally and preferably substituted by 1 to 3 $NH_2$ moieties. The selection of any number of carbon atoms in the hydrocarbon chain can constitute a desirable execution depending upon the choice of additional optional groups and/or optional moieties. The actual determination of preferred combinations is a routine measure, well known in the domain of the technology.

A second essential aminoacid alkylphosphonic acid for use in the method of this invention can be represented by the formula:

$$A^2\text{-}B_y$$

wherein $A^2$ has the formula $$HOOC\text{—}C(NH_2)(R)(R')$$

wherein R and R are independently selected from $C_1$-$C_{20}$ linear, branched, cyclic or aromatic hydrocarbon chains, (said chains being) optionally substituted by $C_1$-$C_{12}$ linear, branched, cyclic or aromatic hydrocarbon groups, (said groups and/or said chains being) optionally substituted by OH, $NH_2$ and/or COOH moieties, and one of R or R' can be hydrogen with the proviso of excluding structures which are not suitable for use within the context of the inventive technology.

In a preferred execution of the method herein, the aminoacid in the phosphonate inhibitor (ii) can be represented by D,L-alanine wherein y is 2, L-alanine wherein y is 2, L-lysine wherein y is in the range of from 2 to 4, L-phenylalanine wherein y is 2, L-arginine wherein y is in the range of from 2-6, L-threonine wherein y is 2, L-methionine wherein y is 2, L-cysteine wherein y is 2 and L-glutamic acid wherein y is 1 to 2.

It was found that the L-glutamic acid alkylene phosphonic acid compound as such is, because of insufficient performance and stability, not suitable for use in the method of this invention. Depending upon the formation reaction conditions, the L-glutamic acid alkylene phosphonic acid resulting from the methylenephosphonation of L-glutamic acid can be represented by a substantially binary mixture containing, based on the mixture (100%), a majority of a mono-methylene phosphonic acid derived from a carboxylic acid substituted pyrrolidone and a relatively smaller level of a dimethylene phosphonic acid glutamic acid compound. It was found that, in one beneficial embodiment the reaction product frequently contains from 50% to 90% of the pyrrolidone carboxylic acid N-methylene phosphonic acid scale inhibitor and from 10% to 50% of the L-glutamic acid bis(alkylene phosphonic acid) compound. The sum of the diphosphonate and monophosphonate inhibitors formed during the reaction frequently exceeds 80%, based on the glutamic acid starting material. The binary mixture can also be prepared by admixing the individual, separately prepared, phosphonic acid compounds. In another preferred execution, the L-lysine carrying one alkylene phosphonic acid group attached to amino radical(s) represents not more than 20 molar % of the sum of the L-lysine carrying one and two alkylene phosphonic acid groups attached to amino radical(s). In another preferred execution, the L-lysine alkylene phosphonic acid is represented by a mixture of L-lysine carrying two alkylene phosphonic acid groups attached to (individual) amino radical(s) (lysine di) and L-lysine carrying four alkylene phosphonic acid groups (lysine tetra) whereby the weight ratio of lysine tetra to lysine di is in the range of from 9:1 to 1:1, even more preferred 7:2 to 4:2.

Preferred aminoacids in the phosphonate inhibitors (i) include 7-aminoheptanoic acid, wherein x is 2, 6-aminohexanoic acid, wherein x is 2, 5-aminopentanoic acid, wherein x is 2, 4-amino butyric acid, wherein x is 2 and β-alanine wherein x is 2. Preferred aminoacids in the phosphonate inhibitors (i) can be prepared beneficially starting from lactams or other conventionally known materials; 7-aminoheptanoic acid can be used instead of 2-azacyclooctanone to make the corresponding diphosphonate. The preferred aminoacid starting materials are illustrated in the examples hereinafter. In short, a mixture of stoichiometric proportions of the starting material aminoacid (1 mole), phosphorous acid (2 moles), aqueous hydrochloric acid (1.2 moles) is heated under stirring to 100° C., the formaldehyde (2 moles) is then gradually added over a period of 120-140 minutes at a temperature in the range of from 100-120° C. The reaction mixture is thereafter kept at 105-115° C. for an additional 60-100 minutes. It is understood that the stoichiometric proportions of the starting materials can be varied to meet the desired degree of phosphonic acid substitution by reaction with the available N—H functions.

In another preferred execution herein, the scale inhibitor for use in the method of this invention can be represented by selected combinations of aminoacid polyphosphonates of this invention in combination with a phosphonic acid selected from the group of: (a) amino(poly)alkylene polyphosphonic acids wherein the alkylene moiety contains from 1 to 20 carbon atoms; (b) hydroxyalkylene polyphosphonic acids wherein the alkylene moiety contains from 2 to 50 carbon atoms; and (c) phosphono alkane polycarboxylic acids wherein the alkane moiety is in straight chain configuration containing from 3 to 12 carbon atoms. Actually preferred are: aminoalkylene polyphosphonic acids having from 1 to 12 carbon atoms in the alkylene moiety; hydroxyalkylene phosphonic acids containing from 2 to 12 carbon atoms in the alkylene moiety and two phosphonic acid groups; whereas phosphono alkane polycarboxylic acids have a straight chain alkane configuration having from 4 to 8 carbon atoms and wherein the molar ratio of phosphonic acid radical to carboxylic acid radical is in the range of from 1:2 to 1:4. Particularly preferred are polyphosphonic acids having from 2 to 8 phosphonic acid groups. Individually preferred species were found to include the following: aminotri(methylene phosphonic acid) and its N-oxide; 1-hydroxyethylene(1,1-diphosphonic acid); ethylenediamine tetra(methylene phosphonic acid); diethylene triamine penta(methylenephosphonic acid); hexamethylene diamine tetra(methylene phosphonic acid); hydroxyethyl aminobis(methylene phosphonic acid); N,N'-bis(3-aminopropyl)-ethylenediamine hexa(methylene phosphonic acid); and butane-2-phosphono-1,2,4-tricarboxylic acid.

The ponderal ratio of aminoacid phosphonate to phosphonic acid is in the range of from 98:2 to 25:75, preferably from 90:10 to 50:50.

$A^2$ can be represented by α-amino acids including specific natural amino acids such as e.g. occurring in animal species. Amino acids generally are the building blocks of proteins. There are over forty known amino acids about twenty of which are actually contained in e.g. animal tissue. Amino acids can be made by hydrolysis starting from proteins, by enzymatic fermentation and/or by chemical synthesis. This domain of the technology is eminently well known and all the individual technologies are abundantly documented in the literature. Suitable amino acids can be used in their D, D,L, and L forms as well as mixtures of the D and L forms. Preferred α-amino acids for use in the phosphonate inhibitors include: D,L-alanine; L-alanine; L-phenylalanine; L-lysine; L-arginine; L-methionine; L-cysteine; L-threonine; and L-glutamic acid.

Specific amino acids are excluded as follows:
1. α-aminoacids wherein R and/or R' are electron rich moieties directly attached to an aromatic moiety. As an example, the reaction of L-tyrosine (1 eq.) (R=-p-OH Phenyl; R'=H) with $H_3PO_3$ (2 eq.) and formaldehyde (2.2 eq.) in the presence of HCl (1.5 moles) between 108 and 112° C. does not lead to the corresponding bis(methylene phosphonic acid). Indeed, $^{31}P$ NMR analysis only shows signals for the starting phosphorous acid with traces of phosphoric acid. A water insoluble product is obtained; it is believed to be due to the reaction of formaldehyde with tyrosine resulting in the formation of methylene bridges between aromatic moieties;
2. α-aminocids wherein R and/or R' are aromatics wherein at least one carbon atom has been substituted by a heteroatom. For example, the reaction of L-tryptophan (1 eq.) with $H_3PO_3$ (2 eq.) and formaldehyde (2.2 eq.) in the presence of HCl (2.5 moles) between 107 and 111° C. does not lead to the corresponding bis(methylene phosphonic acid). $^{31}P$ NMR analysis only shows signals for the starting phosphorous acid with traces of phosphoric acid. A water insoluble product is obtained; it is believed to be due to the reaction of formaldehyde with tryptophan resulting in the formation of methylene bridges between aromatic moieties; and
3. α-aminoacids wherein in the event R is —C(X)(R'')(R''') and R', R'' and R''' are hydrogen wherein X is an electron withdrawing group selected from $NO_2$, CN, COOH, $SO_3H$, OH and halogen. As an example, the reaction of L-aspartic acid (1 eq.) (X=COOH) with $H_3PO_3$ (2 eq.) and formaldehyde (2.2 eq.) in the presence of HCl (1.5 moles) between 110 and 115° C. leads to a complex product mixture including: fumaric acid; imino-bis(methylene phosphonic acid); aminotri(methylene phosphonic acid) (ATMP) and L-aspartic acid bis(methylene phosphonic acid). The latter product has been shown by $^{31}P$ NMR to decompose under the reaction conditions into fumaric acid and imino bis(methylene phosphonic acid) which is itself converted into ATMP. In another example, the reaction of L-serine (1 eq.)(X=OH) with $H_3PO_3$ (2 eq.) and formaldehyde (2.2 eq.) in the presence of HCl (1.5 moles) between 107 and 112° C. leads to a complex product mixture including amino trimethylene phosphonic acid) (ATMP) and phosphorous acid. $^{31}P$ NMR does not show signals corresponding to the L-serine mono- or di-phosphonates. It is believed that the L-serine phosphonates are unstable and decompose, under the reaction conditions, ultimately leading to ATMP.

Specific α-aminoacids not suitable for use within the claimed technology are: tyrosine; tryptophan; asparagine; aspartic acid; and serine.

The amino acid alkylphosphonate scale inhibitors for use in the inventive method can be prepared by reacting one or more of the available N—H functions of the aminoacid with phosphorous acid and formaldehyde, in the presence of hydrochloric acid, in aqueous medium having a pH of generally less than 4 by heating that reaction mixture, at a temperature of usually greater than 70° C. for a sufficient time to complete the reaction. This kind of reaction is conventional and well-known in the domain of the technology and examples of the novel phosphonate compounds have been synthesized, as described below, via the hydrochloric acid route.

In a preferred method, the aminoacid phosphonates can be made under substantial exclusion of hydrohalogenic acid and corresponding by-products and intermediates. Specifically, the aminoacid phosphonates can be manufactured in presence of not more than 0.4%, preferably less than 2000 ppm, of hydrohalogenic acid, expressed in relation to the phosphorous acid component (100%) by reacting:
(a) phosphorous acid;
(b) an aminoacid; and
(c) a formaldehyde:
in reactant ratios of (a):(b) of from 0.05:1 to 2:1; (c):(b) of from 0.05:1 to 5:1; and (c):(a) of from 5:1 to 0.25:1;
wherein (a) and (c) stand for the number of moles to be used and (b) represents the number of moles multiplied by the number of N—H functions in the amine, in the presence of an acid catalyst having a pKa equal or inferior to 3.1, said catalyst being homogeneous with respect to the reaction medium and being used in reactant ratios as follows:
(b):(d) of from 40:1 to 1:5;
wherein (d) stands for the number of moles of catalyst multiplied by the number of available protons per mole of catalyst, followed by recovering the aminoacid phosphonates formed in a manner known per sé.

The catalyst has a pKa equal or inferior to 3.1, preferably equal or inferior to 2.75, most preferably equal or inferior to 1.9, said catalyst being homogeneously compatible with the reaction medium. The pKa can be expressed as follows:

$$pKa = -\log_{10} Ka$$

wherein Ka represents the thermodynamic equilibrium acidity constant.

The term "homogeneous" catalyst means that the catalyst, suitable for use, forms a single liquid phase within the reaction medium under the reaction conditions. The homogeneous nature of a catalyst can be ascertained routinely by e.g. visible inspection of precipitation or phase separation properties.

Preferred catalyst species can be selected from sulphuric acid, sulphurous acid, trifluoroacetic acid, trifluoromethane sulfonic acid, methane sulfonic acid, oxalic acid, malonic acid, p-toluene sulfonic acid and naphthalene sulfonic acid.

The homogenous reaction is preferably conducted at a temperature in the range of from 70° C. to 150° C. with an approach selected from:
  conducting the reaction under ambient pressure with or without distillation of water and non-reacted formaldehyde;
  in a closed vessel under autogeneous pressure built up;
  in a combined distillation and pressure arrangement whereby the reaction vessel containing the reactant mixture is kept under ambient pressure at the reaction temperature followed by circulating the reaction mixture through a reactor operated under autogeneous pressure built up thereby gradually adding the formaldehyde and other selected reactants in accordance with needs; and
  a continuous process arrangement, possibly under autogeneous pressure built up, whereby the reactants are continuously injected into the reaction mixture and the phosphonic acid reaction products is withdrawn on a continuous basis.

In another preferred method, the aminoacid phosphonates for use herein can be prepared under substantial exclusion of hydrohalogenic acid, specifically in the presence of not more than 0.4%, preferably less than 2000 ppm, of hydrohalogenic acid, expressed in relation to the phosphorous acid component (100%), by reacting: (a) phosphorous acid; (b) an aminoacid; and (c) formaldehyde; in reactant ratios as follows: (a):(b) of from 0.05:1 to 2:1; (c):(b) of from 0.05:1 to 5:1; and (c):(a) of from 5:1 to 0.25:1; wherein (a) and (c) stand for the number of moles to be used and (b) represents the number of moles multiplied by the number of N—H functions in the amino acid, in the presence of a heterogeneous, with respect to the reaction medium, Broensted acid catalyst selected from the group consisting of:
(1) solid acidic metal oxide combinations as such or supported onto a carrier material;
(2) cation exchange resins selected from the group comprising copolymers of styrene, ethyl vinyl benzene and divinyl benzene, functionalized so as to graft $SO_3H$ moieties onto the aromatic group and perfluorinated resins carrying carboxylic and/or sulfonic acid groups;
(3) organic sulfonic and carboxylic Broensted acids which are substantially immiscible in the reaction medium at the reaction temperature;
(4) an acid catalyst derived from:
  (i) the interaction of a solid support having a lone pair of electrons onto which is deposited an organic Broensted acid;
  (ii) the interaction of a solid support having a lone pair of electrons onto which is deposited a compound having a Lewis acid site;
  (iii) heterogeneous solids functionalized by chemical grafting with a Broensted acid group or a precursor therefore; and
(5) heterogeneous heteropolyacids of the general formula $H_xPM_yO_z$ wherein P is selected from phosphorus and silicon and M is selected from W and Mo and combinations thereof
followed by recovering the aminoacid alkylphosphonic acid formed in a manner known per sé.

Examples of suitable Broensted catalysts are fluorinated carboxylic acids and fluorinated sulfonic acids having from 6 to 24 carbon atoms in the hydrocarbon chain. A specific example of a suitable catalyst is represented by perfluorinated undecanoic acid.

In another execution, suitable heterogeous acid catalysts can be represented by cation exchange resins. Usually such resins comprise copolymers of styrene, ethylvinyl benzene and divinyl benzene functionalized such as to graft $SO_3H$ groups onto the aromatic groups.

These catalysts can be used in different physical configurations such as in gel form, in a macro-reticulated configuration or supported onto a carrier material such as silica, or carbon, or carbon nanotubes. The heterogeneous Broensted catalyst can be used in many operational manufacturing arrangements well known in the domain of the technology. The term "heterogeneous" means that the Broensted catalyst is substantially insoluble in the reaction medium at the reaction conditions or substantially immiscible, thus liquid, in the reaction medium at the reaction conditions. The heterogeneous reaction is preferably conducted at a temperature in the range of from 70 to 150° C. for a time sufficient to complete the reaction.

The essential formaldehyde component is a well known commodity ingredient. Formaldehyde generally is produced and sold as water solutions containing variable, frequently minor, e.g. 0.3-3%, amounts of methanol and are reported on a 37% formaldehyde basis. Formaldehyde solutions exist as a mixture of oligomers. Formaldehyde precursors can, for example, be represented by paraformaldehyde, a solid mixture of linear poly(oxymethylene glycols) of usually fairly short, n=8-100, chain length, and cyclic trimers and tetramers of formaldehyde designated by the terms trioxane and tetraoxane respectively. The formaldehyde component can also be represented by aldehydes and ketones having the formula $R_1R_2C=O$ wherein $R_1$ and $R_2$ can be identical or different and are selected from the group of hydrogen and organic radicals. When $R_1$ is hydrogen, the material is an aldehyde. When both $R_1$ and $R_2$ are organic radicals, the material is a ketone. Species of useful aldehydes are, in addition to formaldehyde, acetaldehyde, caproaldehyde, nicotinealdehyde, crotonaldehyde, glutaraldehyde, p-tolualdehyde, benzaldehyde, naphthaldehyde and 3-aminobenzaldehyde. Suitable ketone species for use herein are acetone, methylethylketone, 2-pentanone, butyrone, acetophenone and 2-acetonyl cyclohexanone.

The phosphorous acid reactant is preferably prepared, in a known manner, under substantial exclusion of halogen, by contacting elemental phosphorus, such as tetraphosphorus, with water at a temperature below 200° C., in the presence of a catalyst effective to promote oxidation of phosphorus, by reaction with water; or by contacting P(V) species with a reducing agent, such as hydrogen, in the presence of a reducing catalyst; or by contacting a hydrolysis feed mixture comprising phosphate esters and phosphonate esters with liquid water and steam to thereby hydrolyze the phosphonate esters to phosphorous acid.

The syntheses of examples of the amino acid phosphonates herein are described.

165.19 g (1 mole) of L-phenyl alanine are mixed with a solution of 164 g (2 moles) of phosphorous acid in 147.8 g of 37% aqueous hydrochloric acid (1.5 moles) and 250 cc of water. The mixture is heated under stirring to 110° C. 180.5 g of a 36.6% aqueous solution (2.2 moles) of formaldehyde are added over a period of 110 minutes while maintaining the reaction temperature between 106° C. and 107° C. Upon completion of the formaldehyde addition, the reaction mixture is maintained, for an additional 90 minutes, at a temperature of 107° C. to 108° C. $^{31}P$ NMR analysis of the crude product showed the presence of 68% of L-phenyl alanine bis(methylene phosphonic acid).

131.17 g (1 mole) of L-isoleucine are mixed with a solution of 164 g (2 moles) of phosphorous acid in 147.8 g of 37% aqueous hydrochloric acid (1.5 moles) and 150 cc of water. The mixture is heated under stirring to 110° C. 180.5 g of a 36.6% aqueous solution of formaldehyde (2.2 moles) are added over a period of 100 minutes while maintaining the reaction temperature at 110° C. Upon completion of the formaldehyde addition, the reaction mixture is maintained at 110° C. for an additional 110 minutes. $^{31}P$ NMR analysis of the crude product showed the presence of 69.7% of L-isoleucine bis(methylene phosphonic acid).

131.17 g (1 mole) of D,L-leucine are mixed with a solution of 164 g (2 moles) of phosphorous acid in 147.8 g of aqueous hydrochloric acid (1.5 moles) and 150 cc of water. The mixture is heated, under stirring, to 105° C. 180.5 g of a 36.6% aqueous solution of formaldehyde (2.2 moles) are then added over a period of 100 minutes while maintaining the reaction temperature between 105° C. and 110° C. Upon completion of the formaldehyde addition, the reaction mixture is maintained at 110° C. for an additional 60 minutes. $^{31}P$ NMR analysis of the crude product showed the presence of 69.7% of D,L-leucine bis(methylene phosphonic acid).

117.15 g (1 mole) of L-valine are mixed with a solution of 164 g (2 moles) of phosphorous acid in 147.8 g of 37% hydrochloric acid (1.5 moles) and 150 g of water. The mixture is heated, under stirring, to 110° C. 180.5 g of 36.6% aqueous formaldehyde (2.2 moles) are added in 85 minutes while maintaining the reaction temperature at 107° C. Upon completion of the formaldehyde addition, the reaction mixture is maintained at 107° C. for an additional 60 minutes. $^{31}P$ NMR analysis of the reaction product, as is, showed the presence of 70.3% of L-valine bis(methylene phosphonic acid).

85 g (1 mole) of 2-pyrrolidone are mixed with a solution of 164 g (2 moles) of phosphorous acid in 118.4 g of 37% hydrochloric acid (1.2 moles) and 100 g of water. The mixture is heated, under stirring, to 100° C. 172.1 g of 36.6% aqueous formaldehyde (2.1 moles) are added over a period of 135 minutes while maintaining the reaction temperature between 100° C. and 114° C. Upon completion of the formaldehyde addition, the reaction mixture is maintained at 110° C. for an additional 90 minutes. $^{31}P$ NMR analysis of the reaction product, as is, showed the presence of 91.2% of 4-amino butanoic acid bis(methylene phosphonic acid).

113.1 g (1 mole) of ε-Caprolactam are mixed with 164 g (2 moles) of phosphorous acid in 118.4 g of 37% aqueous hydrochloric acid (1.2 moles) and 100 g of water. The mixture is heated, under stirring, to 100° C. 172.1 g of 36.6% aqueous formaldehyde (2.1 moles) are added over a period of 105 minutes while maintaining the reaction temperature between 100° C. and 112° C. Upon completion of the formaldehyde addition, the temperature of the reaction mixture is maintained, for an additional 75 minutes, at a temperature of 110° C. $^{31}P$ NMR analysis of the reaction product showed the presence of 89% of 6-amino hexanoic acid bis(methylene phosphonic acid).

92.27 g (0.65 mole) of 2-Azacyclononanone are mixed with 106.6 g (1.3 moles) of phosphorous acid in 96.07 g of 37% aqueous hydrochloric acid (0.97 mole) and 65 g of water. The mixture is heated, under stirring, to 100° C. 114 g of 36.6% aqueous formaldehyde (1.39 moles) are then added in 70 minutes while maintaining the reaction temperature between 104° C. to 106° C. Upon completion of the formaldehyde addition, the temperature of the reaction mixture is maintained at 107° C. for an additional 60 minutes. $^{31}P$ NMR analysis of the reaction product showed the presence of 84% of 8-amino octanoic acid bis(methylene phosphonic acid).

89 g (1 mole) of L-alanine are mixed with 164 g (2 moles) of phosphorous acid in 147.81 g of 37% aqueous hydrochloric acid (1.5 moles) and 150 g of water. The mixture is heated, under stirring, to 110° C. 180.51 g of 36.6% aqueous formaldehyde (2.2 moles) are then added over a period of 120 minutes while maintaining the temperature of the reaction mixture between 110° C. and 115° C. Upon completion of the formaldehyde addition, the temperature of the reaction mixture is maintained at 106° C. for an additional 60 minutes. $^{31}P$ NMR analysis of the reaction product showed the presence of 77.6% of L-alanine bis(methylene phosphonic acid).

Arginine was reacted, in a conventional manner, with phosphorous acid and formaldehyde in the presence of hydrochloric acid. The crude reaction was found to be substantially completely, 72.7%, represented by a bis(alkylene phosphonic acid) derivative. This reaction product was used in the Examples.

91.33 g (0.5 mole) of L-lysine hydrochloride are mixed with 164 g (2 moles) of phosphorous acid in 73.91 g of 37% aqueous hydrochloric acid (0.75 mole) and 120 g of water. The mixture is heated, under stirring, to 105° C. 180.51 g of 36.6% aqueous formaldehyde (2.2 moles) are added over a period of 120 minutes while maintaining the reaction temperature between 106° C. and 109° C. Upon completion of the formaldehyde addition, the temperature of the reaction mixture is maintained at 106° C. for an additional 50 minutes. $^{31}P$ NMR analysis of the reaction product showed the presence of 72.2% of L-lysine tetra(methylene phosphonic acid) and about 14% of 2-amino 6-imino bis(methylene phosphonic acid) hexanoic acid. This preparation was used in the Examples under the name "tetraphosphonate".

273.98 g (1.5 moles) of L-lysine hydrochloride are mixed with 369 g (4.5 moles) of phosphorous acid in 221.72 g of 37% aqueous HCl (2.25 moles) and 400 g of water. The mixture is heated with stirring to 106° C. 404.14 g of 36.6% Aqueous formaldehyde (4.95 moles) are added over a period of 180 minutes while maintaining the reaction temperature between 106 and 112° C. Upon completion of the formaldehyde addition, the reaction mixture is heated for an additional 60 minutes at 110° C. $^{31}$P NMR analysis of the crude product shows the presence of 52.1% of L-lysine tetra(methylene phosphonic acid), about 19.7% of 2-amino-6-imino bis(m-ethylene phosphonic acid)hexanoic acid and about 22% of N-Me L-lysine diphosphonate. This composition corresponds to an approximate average of 2 methylene phosphonic acid groups per L-lysine moiety. This preparation was used in the Examples under the name "diphosphonate".

147.13 g (1 mole) of L-glutamic acid are mixed with a solution of 164 g (2 moles) of phosphorous acid in 147.8 g of 37% aqueous HCl (1.5 moles) and 120 ml of water. This mixture is heated, under stirring, to 110° C. 180.5 g of 36.6% Aqueous formaldehyde (2.2 moles) are added over a period of 105 minutes while maintaining the reaction temperature around 110° C. Upon completion of the formaldehyde addition, the temperature of the reaction mixture is maintained at 110° C. for an additional 30 minutes. $^{31}$P NMR analysis of the reaction product shows the presence of 20.1% of L-glutamic acid bis(methylene phosphonic acid) and 51.5% of 2-pyrrolidone-5-carboxylic acid N-methylene phosphonic acid.

Scale formation, such as carbonate and sulphate scales, can be a major problem in oil field production facilities that can result in a significant well productivity decline. This can, in particular, apply when sea water is injected into the oil bearing formation to compensate e.g. for a loss in gas pressure. As a result of the presence of important quantities of barium and calcium ions in the down-hole formation water, calcium sulphate and especially barium sulphate and strontium sulphate can become a major problem in the operation of the well. Whereas sulphate scales prevail upon seawater injection during the enhanced oil recovery treatment, milder pH conditions, prevailing closer to the surface, pressure differences and high temperatures in the down-hole formation usually lead to the formation of mixtures of carbonate and sulphate scale. The scale inhibitors shall therefore exhibit performance over a broad range of conditions such as can occur in the oil wells and production facilities. The inhibitor can be introduced into the oil bearing formation by any suitable treatment including a "squeeze" treatment. In general such a method for oil recovery requires injecting into a marine oil well an aqueous solution of the aminoacid phosphonic acid scale inhibitor of this invention in a usual level of from 0.1 to 100000 ppm. Frequently, the production oil well activity is stopped and the inhibitor solution is injected into the oil well formation. It was established that the scale inhibitors in accordance with this invention can be used effectively and singly. The squeeze treatment generally consists of injecting a scale inhibitor solution into the wellbore of the producing well to place the inhibitor into the formation. The scale inhibitor released from the formation is present, in the return water, in a concentration of, at least, 0.1, usually at least 0.5, frequently from 10 to 100 ppm to thus exhibit effective scale control and consequently secure oil well production continuity with levels of inhibitor means reduced by one order of magnitude compared to actually prevailing practice.

In more detail, a beneficial method for oil recovery can be done by injecting into marine oil wells an aqueous solution of the aminoacid phosphonic acid compound of the invention in a level of from 0.1 to 100000 ppm. The method can be conducted by continuously injecting into the well an aqueous solution of from 0.1 to 800 ppm of the aminoacid phosphonic acid compound. The continuous injection frequently means that the scale inhibitor solution is injected into the water injection well. However, it is understood that the continuous injection can also apply to the surroundings of the production well such as the well-head arrangement including underwater equipment for example pumps and pipes. The aminoacid scale inhibitors of this invention can also be used in squeeze oil recovery methods. Such squeeze method comprises, in sequence: stopping the production wellbore activity; introducing through the production wellbore the aqueous treatment solution containing the aminoacid phosphonic acid scale inhibitor in a level of from 100 to 100000 ppm; injecting sea water through the production wellbore to place the scale inhibitor within the targeted area of the formation; restarting the oil extraction activity; and producing return fluids, containing oil and return water, through the production wellbore.

The inventive method also contemplates the use of the aminoacid phosphonic acid inhibitors herein in scale forming water systems containing usually more than 100 mg/l of barium and/or strontium hardness and/or calcium carbonate and having a pH generally within the range of from 2-10. To that effect, of from 0.1 to 800 ppm, preferably of from 0.2 to 100 ppm, of the aminoacid phosphonate scale inhibitor is added to the water system.

The individual aminoacid phosphonate scale inhibitors can, in one execution, be used substantially singly, or in the event they are used as a mixture of more than one (i) species or a mixture of more than one (ii) species or as a mixture of (i) and (ii) species, then it was observed that one individual inhibitor in accordance with this invention shall constitute, on a ponderal basis, at least 50%, usually 60% or more of the mixture of inhibitors of this invention. It was observed that aminoacid mixtures originating from protein hydrolysates are not well suitable for use in the method herein due to, inter alia, interactions of the various species which can adversely affect performance. Preferred scale inhibitors herein, particularly for application within the context of oil producing wells, shall have a thermal decomposition, measured at 140° C., of less than about 10%.

The scale inhibitor performance of the aminoacid alkyl phosphonates suitable for use in the method of this invention can be quantified thereby using comparative testing methods as follows.

Thermal Stability Assessment.

This is a test to assess the thermal stability of phosphonates in the presence of synthetic North Sea water. The test is carried out by submitting mixtures of North Sea water and phosphonates stabilized at pH 5.5 to a one week heating at 140° C. The thermal degradation is determined by $^{31}$P NMR analysis. The results give the percentage by weight of product which is decomposed after the treatment.

Test details are as follows:
prepare an aqueous solution containing 20% of active acid phosphonate (AA) at pH 5.5 (solution 1);
prepare synthetic North Sea water having a pH of 5.5 (solution 2);
prepare a sample of 1% active acid phosphonate by mixing 1 g of solution 1 with 19 g of solution 2;
put the sample so prepared in an oven at 140° C. for one week; and analyze the sample, after the heat treatment, for thermal decomposition by means of $^{31}P$ NMR spectroscopy.

Brine/Sea Water Compatibility.

This test assesses sea water compatibility of the phosphonates added at: 100; 1000; 10000; and 50000 ppm to North Sea water after 22 hours at 90° C. Calcium left in solution is measured by ICP.

Test details are as follows:
prepare synthetic North Sea water at pH 5.5;
add the phosphonate at 100, 1000, 10000 and 50000 ppm active acid to the synthetic North Sea water solution;
prepare 5 blank solutions made by mixing the required amount of distilled water with North Sea water to obtain the same dilution as obtained by the addition of 1, 100, 1000, 10000 and 50000 ppm active acid phosphonate to the synthetic North Sea water solution;
the phosphonate samples with the respective phosphonates at the 4 concentrations as well as the 5 blanks are stored in an oven at 90° C. for a period of 22-24 hours;
upon completion of the test, the samples are observed visually;
after completion of the test, the pH values are being carefully monitored and 50 ml are drawn from each sample, filtered through a 40 μm Millipore filter and stabilized at pH<2 by addition of 37% aqueous hydrochloric acid;
Ca tolerance values are calculated as follows:

$$\% \ Ca \ \text{tolerance} = \frac{V_1}{V_0} \times 100$$

where $V_0$=ppm Ca found in the blank solution; and
$V_1$=ppm Ca found in the solution with the phosphonate.

Barium Sulphate Scale Inhibition.

This is a static test to evaluate the efficiency of phosphonates in preventing barium and strontium scale inhibition in oil field scaling conditions. The test is carried out by determining the amount of $BaSO_4$ and $SrSO_4$ that has precipitated after 22 hours at 90° C. in a 50/50 mixture of synthetic North Sea water and Formation water containing the phosphonates to be tested at 5 different concentrations. The amount of soluble Ba and Sr ions is determined by ICP. The results stand for the minimum phosphonate concentration for 100% barium sulphate scale inhibition or give the scale inhibition at 100 ppm loading of phosphonate.

Test details are as follows:
Synthetic North Sea Water:

| Salts | mmol/l |
|---|---|
| NaCl | 420.1 |
| $CaCl_2 \cdot 2H_2O$ | 10.08 |
| $MgCl_2 \cdot 6H_2O$ | 54.32 |
| KCl | 8.7 |
| $Na_2SO_4 \cdot 10H_2O$ | 25.8 |
| $NaHCO_3$ | 2.21 |

Formation Water:

| Salts | mmol/l |
|---|---|
| NaCl | 1313 |
| $CaCl_2 \cdot 2H_2O$ | 77.75 |
| $MgCl_2 \cdot 6H_2O$ | 19.74 |
| KCl | 11 |
| $BaCl_2 \cdot 2H_2O$ | 1.82 |
| $SrCl_2 \cdot 6H_2O$ | 7.53 | synthetic North Sea and Formation water are prepared having a pH of 6. These water solutions are preheated at 90° C. before starting the test. An acetic acid/sodium acetate buffer is prepared and added to the North Sea water in order to give the required pH;
add to a glass bottle the required amount of scale inhibitor to obtain the test concentrations (15, 30, 50, 70 and 100 ppm active phosphonic acid) of the scale inhibitor in the final test mixture;
to this glass bottle, add 50 ml of North Sea water while stirring. Then add to this glass bottle 50 ml of Formation water;
also prepare one blank solution by mixing 50 ml of North Sea water with 50 ml of Formation water;
put the sample bottles in an oven for 22 hours at 90° C.;
after 22 hours, take 3 ml of each test solution from the surface, filter through a 0.45 μm Millipore filter and add to a stabilizing solution. The samples are then analyzed by ICP for Ba and Sr;
the phosphonate efficiencies as $BaSO_4$ and $SrSO_4$ scale inhibition are calculated as follows:

$$\% \ \text{Scale inhibition} = \frac{V_1 - V_0}{V_2 - V_0} \times 100$$

where
$V_0$=ppm Ba (or Sr) found in the blank solution;
$V_1$=ppm Ba (or Sr) found in the solution with the inhibitor;
$V_2$=ppm Ba (or Sr) present in the Formation water.

Scale inhibitor phosphonate samples for use in the method of this invention were performance tested by means of the foregoing testing procedures. The performance data were as follows.

EXAMPLES

| N° (ppm) | Amino Acid | Ba Scale (***) Inhibition | Ca Tolerance in % | | | |
|---|---|---|---|---|---|---|
| | | | 100 | 1000 | 10000 | 50000 |
| 1 | D,L-alanine | 97% @ 100 ppm | 100 | 99 | 94 | 100 |
| 2 | L-alanine | 96% @ 100 ppm | 96 | 90 | 8 | 97 |
| 3 | L-glutamic acid | 31% @ 100 ppm | 100 | 97 | 99 | 97 |

-continued

| N° | (ppm) Amino Acid | Ba Scale (***) Inhibition | Ca Tolerance in % | | | |
|---|---|---|---|---|---|---|
| | | | 100 | 1000 | 10000 | 50000 |
| 4 | L-lysine (*) | 50 ppm full scale | 100 | 81 | 20 | 98 |
| 5 | L-lysine (**) | 30 ppm full scale | 98 | 86 | 27 | 97 |
| 6 | L-phenyl alanine | 10 ppm full scale | 96 | 76 | 1 | 26 |
| 7 | L-isoleucine | 85% @ 100 ppm | 93 | 96 | 44 | 82 |
| 8 | L-histidine | 90% @ 100 ppm | 100 | 100 | 95 | 100 |
| 9 | L-valine | 47% @ 100 ppm | 97 | 98 | 73 | 80 |
| 10 | L-arginine | 30 ppm full scale | 97 | 86 | 6 | 61 |
| 11 | L-threonine | 30 ppm full scale | 94 | 86 | 22 | 85 |
| 12 | L-methionine | 50 ppm full scale | 96 | 77 | 2 | 31 |
| 13 | L-cysteine | 50 ppm full scale | 96 | 99 | 91 | 79 |
| 14 | β-Alanine | 50 ppm full scale | 100 | 98 | 89 | 64 |
| 15 | 4-Amino butyric acid | 21% @ 100 ppm | 97 | 99 | 99 | 100 |
| 16 | 5-Amino pentanoic acid | 13% @ 100 ppm | 100 | 96 | 99 | 100 |
| 17 | 6-Amino hexanoic acid | 12% @ 100 ppm | 98 | 100 | 100 | 100 |
| 18 | 7-Amino heptanoic acid | 11% @ 100 ppm | 99 | 100 | 100 | 100 |

(*) = tetraphosphonate;
(**) = diphosphonate.
(***) expressed as: ppm phosphonate needed for 100% $BaSO_4$ scale inhibition; or % scale inhibition for 100 ppm phosphonate.

A series of phosphonate inhibitors were tested for thermal stability thereby using the method set forth above. The testing results were as follows.

| Example N° | Amino Acid | Thermal Stability at 140° C. 1 week Decomposition in % |
|---|---|---|
| 19 | D,L-alanine | 8.2 |
| 20 | L-alanine | 7.9 |
| 21 | L-glutamic acid | 0 |
| 22 | L-lysine (*) | 2.5 |
| 23 | L-lysine (**) | 8.8 |
| 24 | L-phenylalanine | 4.3 |
| 25 | D,L-leucine | 2.9 |
| 26 | L-isoleucine | 32.3 |
| 27 | L-valine | 19.5 |
| 28 | L-arginine | 18.4 |
| 29 | L-methionine | 6.5 |
| 30 | 4-Amino butyric acid | 30.0 |
| 31 | 5-Aminopentanoic acid | 10.2 |
| 32 | 6-Aminohexanoic acid | 3.5 |
| 33 | 7-Aminoheptanoic acid | 5.4 |
| 34 | Diethylene triamino pentamethylene phosphonate | 23.6 |

(*) = tetraphosphonate;
(**) = diphosphonate.

The performances of a series of aminoacid phosphonate/phosphonic acid scale inhibitor combinations were tested by means of the foregoing testing procedures. The testing data are summarized in the following table. The cumulative weight of the aminoacid phosphonate and the phosphonic acid (ATMP) is 100% e.g. the presence of 30% ATMP means that the aminoacid phosphonate represents 70%.

| Example N° | Amino acid | ATMP % | Ba Scale (***) Inhibition | Ca Tolerance in % | | | |
|---|---|---|---|---|---|---|---|
| | | | | 100 | 1000 | 10000 | 50000* |
| 35 | D,L-alanine | — | 97% @ 100 ppm | 100 | 99 | 94 | 100 |
| 36 | D,L-alanine | 15 | 50 ppm full scale | 100 | 100 | 71 | 93 |
| 37 | D,L-alanine | 30 | 15 ppm full scale | 100 | 98 | 89 | 89 |
| 38 | L-glutamic acid | — | 31% @ 100 ppm | 100 | 97 | 99 | 97 |
| 39 | L-glutamic acid | 15 | 100 ppm full scale | 100 | 100 | 100 | 100 |
| 40 | L-glutamic acid | 30 | 70 ppm full scale | 100 | 100 | 100 | 100 |

| Example N° | Amino acid | ATMP % | Ba Scale (***) Inhibition | Ca Tolerance in % | | | |
|---|---|---|---|---|---|---|---|
| | | | | 100 | 1000 | 10000 | 50000* |
| 41 | 4-Amino butyric acid | — | 21% @ 100 ppm | 97 | 99 | 99 | 100 |
| 42 | 4-Amino butyric acid | 15 | 100 ppm full scale | 97 | 96 | 100 | 100 |
| 43 | 4-Amino butyric acid | 30 | 50 ppm full scale | 100 | 100 | 97 | 100 |
| 44 | 5-Amino pentanoic acid | — | 12% @ 100 ppm | 98 | 100 | 100 | 100 |
| 45 | 5-Amino pentanoic acid | 30 | 70 ppm full scale | 99 | 98 | 100 | 100 |
| 46 | 6-Amino heptanoic acid | — | 11% @ 100 ppm | 99 | 100 | 100 | 100 |
| 47 | 7-Amino heptanoic acid | 30 | 50 ppm full scale | | | | |

*= expressed in ppm.
(***) as in Examples 1-18.

The invention claimed is:

1. A method for oil recovery comprising the step of injecting into marine oil wells an aqueous solution of an aminoacid phosphonic acid scale inhibitor in a level of from 0.1 to 100000 ppm, where the scale inhibitor is selected from the group consisting of:

i. aminoacid alkylphosphonic acids having the formula $$A^1\text{-}(B)_x$$

wherein $A^1$ has the formula $$HOOC\text{-}A\text{-}NH_2$$

wherein A is independently selected from $C_2$-$C_{20}$ linear, branched, cyclic or aromatic hydrocarbon chains, optionally substituted by $C_1$-$C_{12}$ linear, branched, cyclic or aromatic hydrocarbon groups, optionally substituted by OH, COOH and/or $NH_2$ moieties, and B is an alkylphosphonic acid moiety having from 1 to 6 carbon atoms in the alkyl group and x is an integer of from 1 to 10, and ii. aminoacid alkylphosphonic acids having the formula $$A^2\text{-}B_y$$

wherein $A^2$ has the formula $$HOOC\text{---}C(NH_2)(R)(R')$$

wherein R and R' are independently selected from $C_1$-$C_{20}$ linear, branched, cyclic or aromatic hydrocarbon chains, optionally substituted by $C_1$-$C_{12}$ linear, branched, cyclic or aromatic $NH_2$ and/or COOH, and one of R or R' can be hydrogen with the proviso of excluding:

compounds wherein R and/or R' are electron rich moieties containing, at least, one lone pair of electrons, which moiety is directly attached to an aromatic moiety by a covalent bond; or aromatics wherein at least one of the carbon atoms has been substituted by a heteroatom; and compounds, in the event R is —C(X)(R")(R''') and R', R" and R''' are hydrogen wherein X is an electron withdrawing group selected from $NO_2$, CN, COOH, $SO_3H$, OH and halogen, and with the further proviso that when:

$A^2$ is L-lysine, at least one L-lysine amino radical carries 2 (two) alkyl phosphonic acid moieties; and when $A^2$ is L-glutamic acid, the term glutamic acid phosphonate represents a combination of from 50-90% by weight pyrrolidone carboxylic acid N-methylene phosphonic acid and from 10-50% by weight of L-glutamic acid diphosphonic acid, expressed on the basis of the reaction products; and B is an alkylphosphonic acid moiety having from 1 to 6 carbon atoms in the alkyl group and y is an integer in the range of from 1 to 10.

2. The method for oil recovery in accordance with claim 1 wherein an aqueous solution containing of from 0.1 to 800 ppm of the aminoacid phosphonic acid compound is continuously injected into the well.

3. The method for oil recovery in accordance with claim 1 comprising, in sequence: stopping the production wellbore activity; introducing through the production wellbore the aqueous treatment solution comprising the aminoacid phosphonic acid scale inhibitor in a level of from 100 to 100000 ppm; injecting sea water through the production wellbore to place the scale inhibitor within the targeted area of the formation; restarting the oil extraction activity; and producing return fluids, containing oil and return water, through the production wellbore.

4. The method in accordance with claim 1 wherein the scale inhibitor is selected from the group of:

i. aminoacid alkylphosphonic acids having the formula $$A^1\text{-}(B)_x$$

wherein $A^1$ is
7-aminoheptanoic acid;
6-aminohexanoic acid;
5-aminopentanoic acid;
4-aminobutyric acid; and
β-alanine;

B is an alkylphosphonic acid moiety having from 1 to 6 carbon atoms in the alkyl group and x is 2 in each of such species;

and from the group of:

ii. aminoacid alkylphosphonic acids having the formula $$A^2\text{-}B_y$$

wherein $A^2$ is
α-alanine;
L-lysine;
L-glutamic acid;
L-phenylalanine;
L-methionine; and
L-cysteine;

with the proviso that when:

A² is L-lysine, at least one L-lysine amino radical carries 2 (two) alkyl phosphonic acid moieties; and when A² is L-glutamic acid, the term glutamic acid phosphonate represents a combination of from 50-90% by weight pyrrolidone carboxylic acid N-methylene phosphonic acid and from 10-50% by weight of L-glutamic acid diphosphonic acid, expressed on the basis of the reaction products; and B is an alkylphosphonic acid moiety having from 1 to 6 carbon atoms in the alkyl group and y is from 2 to 4 for L-lysine, y is from 1 to 2 for L-glutamic acid and y is 2 in each of the other species;

said inhibitor being present, in the return water, in a level of from 0.1 to 20 ppm.

5. The method in accordance with claim 1 whereby in the event a mixture of the scale inhibitors is used one of the individual scale inhibitors shall constitute, on a ponderal basis, 60% by weight or more of the ponderal sum of the total scale inhibitors.

6. The method in accordance with claim 1 wherein the scale inhibitor has a thermal stability, measured at 140° C., of at least about 90% by weight, whereby the aminoacid moiety in said scale inhibitor is selected from the group of α-alanine, L-glutamic acid, L-lysine, L-phenylalanine, D,L-leucine, L-methionine, 5-aminopentanoic acid, 6-aminohexanoic acid and 7-aminoheptanoic acid, said aminoacid moieties being attached to two alkylphosphonic acid moieties, except L-lysine containing from 2 to 4 alkylphosphonic acid moieties and L-glutamic acid containing 1 to 2 alkylphosphonic acid moieties.

7. The method in accordance with claim 1 wherein the L-lysine alkylene phosphonate is represented by a mixture of L-lysine di(alkylene phosphonic acid) and L-lysine tetra (alkylene phosphonic acid) whereby the weight ratio of L-lysine tetra(alkylene phosphonic acid) to L-lysine di(alkylene phosphonic acid) is in the range of from 9:1 to 1:1.

8. The method in accordance with claim 7 wherein the weight ratio of lysine tetra(alkylene phosphonic acid) to L-lysine di(alkylene phosphonic acid) is in the range of from 7:2 to 4:2.

9. The method in accordance with claim 1 wherein L-lysine carrying one alkylene phosphonic acid group attached to amino radical(s) represents not more than 20 molar % of the sum of L-lysine carrying one and two alkylene phosphonic acid groups attached to amine radicals.

* * * * *

UNITED STATES PATENT AND TRADEMARK OFFICE
CERTIFICATE OF CORRECTION

PATENT NO.       : 8,461,088 B2  Page 1 of 1
APPLICATION NO. : 12/376896
DATED            : June 11, 2013
INVENTOR(S)      : Notte et al.

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 537 days.

Signed and Sealed this
Eighth Day of September, 2015

Michelle K. Lee
*Director of the United States Patent and Trademark Office*